(12) United States Patent
Colin et al.

(10) Patent No.: US 9,447,371 B2
(45) Date of Patent: Sep. 20, 2016

(54) HOLDER FOR CULTURE PLATES WITH DE-NESTING FEATURE

(75) Inventors: Bruno Colin, Marcy L'Etoile (FR); Yaneli Iakimova, Balan (FR); Kevin G. Ketsenburg, O'Fallon, MO (US); David M. Robbins, Lake Saint Louis, MO (US); Stéphane Bellet, Saint Denis en Bugey (FR)

(73) Assignee: BIOMERIEUX, INC., Durham, NC (US)

( * ) Notice: Subject to any disclaimer, the term of this patent is extended or adjusted under 35 U.S.C. 154(b) by 1762 days.

(21) Appl. No.: 12/221,755

(22) Filed: Aug. 5, 2008

(65) Prior Publication Data

US 2010/0035338 A1 Feb. 11, 2010

(51) Int. Cl.
*C12M 3/00* (2006.01)
*C12M 1/22* (2006.01)
*G01N 35/04* (2006.01)

(52) U.S. Cl.
CPC ............ *C12M 23/48* (2013.01); *C12M 23/10* (2013.01); *G01N 35/04* (2013.01); *G01N 2035/042* (2013.01); *G01N 2035/0425* (2013.01)

(58) Field of Classification Search
CPC ..... C12M 23/10; C12M 23/48; G01N 35/04; G01N 2035/0425; G01N 2035/042
USPC ................. 435/287.3, 283.1–309.4
See application file for complete search history.

(56) References Cited

U.S. PATENT DOCUMENTS

| | | | |
|---|---|---|---|
| 1,576,010 A | 3/1926 | Swartz | |
| 2,226,308 A * | 12/1940 | Gibbs | 312/71 |
| 4,287,301 A | 9/1981 | Astle | 435/30 |
| 4,529,101 A | 7/1985 | Orlowski | 221/11 |
| 4,867,632 A * | 9/1989 | Provan et al. | 414/797.7 |
| 4,909,412 A | 3/1990 | Cerf | 221/1 |
| 5,176,494 A | 1/1993 | Nigrelli et al. | 414/795.6 |
| 5,328,052 A | 7/1994 | Kizilos | 221/42 |
| 5,738,246 A * | 4/1998 | Chung | 221/222 |
| 6,617,146 B1 | 9/2003 | Naccarato et al. | 435/243 |
| 6,913,433 B2 * | 7/2005 | Riesterer et al. | 414/795.6 |
| 7,344,878 B2 | 3/2008 | Lemonnier | 435/305.4 |
| 7,673,773 B1 * | 3/2010 | Walsh et al. | 221/270 |
| 2005/0194397 A1 * | 9/2005 | Hecht | 221/223 |

(Continued)

FOREIGN PATENT DOCUMENTS

| | | | |
|---|---|---|---|
| EP | 1 018 544 | 7/2000 | C12M 1/00 |
| EP | 1018544 A1 * | 7/2000 | |
| JP | 01-168198 | 11/1989 | |
| WO | WO 02/057405 | 7/2002 | C12M 1/22 |

OTHER PUBLICATIONS

International Search Report and Written Opinion dated Jun. 25, 2010 in PCT/US2009/003013 filed May 13, 2009.

*Primary Examiner* — Gautam Prakash
(74) *Attorney, Agent, or Firm* — McDonnell Boehnen Hulbert & Berghoff LLP (57) ABSTRACT

A holding structure for holding a plurality of culture plates in a stacked arrangement includes a feature for de-nesting the bottom culture plate from the plate above it. The de-nesting feature is preferably a structure which urges a plate to move laterally relative to the plate above it. The de-nesting of the bottom culture plate from the adjacent culture plate facilitates withdrawal of the bottom culture plate from the base via a robotic plate transfer mechanism. The de-nesting feature can be entirely passive, such as ramps formed in the base of the holding structure.

13 Claims, 8 Drawing Sheets

(56) References Cited

U.S. PATENT DOCUMENTS

2006/0157493 A1* 7/2006 Christoffersen et al. ....... 221/36
2007/0090125 A1* 4/2007 Njaastad ...................... 221/309
2007/0202564 A1 8/2007 Glasson et al. ................ 435/30
2008/0318310 A1 12/2008 Dufresne et al. .......... 435/309.1

* cited by examiner

HOLDER FOR CULTURE PLATES WITH DE-NESTING FEATURE

BACKGROUND

This invention relates to the field of automated instruments designed for handling culture plates, also known in the art as agar plates.

In the field of microbiology, automated instruments are known which streak a specimen onto a growth medium such as agar which is placed within a culture plate. The culture plate is typically in the form of a Petri dish. The streaked plate is then incubated. The presence of microbial colonies in the plate after incubation indicates that the microbe was present in the original specimen. Instruments for handling culture plates and streaking specimens onto a growth medium are described in U.S. Pat. No. 4,287,301; U.S. Pat. No. 6,617,146 and U.S. patent application publication 2007/0202564. The content of these patent documents is incorporated by reference herein.

In a lab where an instrument such as described in the above-referenced patent documents is installed, a lab technician typically is working with many plates at a time, retrieving plates from refrigerated storage, sorting them, etc., and otherwise manually handling them on the lab bench. Manufacturers of culture plates typically provide features in the bottoms of the plates and in the lids of the plates such that the plates can be nested, and thus stacked one on top of the other, without the plates sliding all around and falling over. For example, the outer edge of the bottom of the plate is sized and shaped so as to just fit within the cover or lid for the plate. That way, a group of plates can be nested and stacked on top of each other, either right-side up (cover up) or upside down (cover down).

SUMMARY OF THE INVENTION

The present inventors have appreciated that the nesting of culture plates can cause problems with a robotic system within a plate handling instrument which removes a plate automatically from a stack of plates. Basically, the nesting of the plates can cause the robotic system to jam. This invention provides for a structure for holding and handling a stack of culture plates and method of operation for withdrawing a plate from the structure, which provides for a de-nesting of culture plates automatically within the structure, thereby facilitating handling of the plates. In particular, the de-nesting features provided by this invention facilitate robotic handling of culture plates in a plate handling instrument without jamming, since the nesting condition is disrupted prior to the robotic system engaging the plate and removing it from the cassette.

In one embodiment, a structure is provided for holding a plurality of culture plates in a stacked arrangement. The holding structure can take the form of an elongated tubular part, referred to herein as a cassette, or it can take the form of a plurality of guide rods which serve to define a region wherein plates can be stacked within the guide rods. The stacked arrangement of culture plates includes a bottom plate. The culture plates contain nesting features wherein one culture plate is in a nested relationship with an adjacent culture plate in the stacked arrangement. The structure holding the stacked arrangement of culture plates includes a base. The base defines an opening wherein the bottom culture plate may be withdrawn from the structure. The base may be integral with the structure or may be a separate piece which is mechanically joined or fastened to the holding structure.

The base includes a feature to de-nest the bottom culture plate from the adjacent culture plate thereby facilitating withdrawal of the bottom culture plate from the base via the opening. The de-nesting feature is preferably passive—i.e., no moving parts are required. For example, the de-nesting feature may take the form of a projection, e.g., sloped ramp, which is provided in the interior of the base which serves to move a plate laterally relative to the plates above it when the plate descends to the bottom position within the cassette. This lateral movement, relative to the plate above it, de-nests the plate. Thus, the ramp or other de-nesting feature automatically disrupts the nesting of the bottom culture plate relative to the plate above it. The robotic plate transfer mechanism may withdraw the bottom plate from the opening of the base. In particular, since the de-nesting of the bottom plate is disrupted, the robotic transfer mechanism can perform its removal operation without jamming or disruption to subsequent processes.

In another aspect, an automated instrument for processing culture plates is provided. The instrument includes a structure such as a cassette or guide rods for holding a plurality of culture plates in a stacked arrangement. The stacked arrangement of culture plates includes a bottom plate. The holding structure holds the stacked arrangement of culture plates in a vertical orientation. The holding structure has a base. The base defines an opening wherein the bottom culture plate in the stack may be withdrawn from the cassette. The culture plates contain nesting features wherein one culture plate is nested in relationship to an adjacent culture plate in the stacked arrangement. The base includes a feature to de-nest the bottom culture plate from the adjacent culture plate thereby facilitating withdrawal of the bottom culture plate from the base via the opening. The instrument further includes a robotic transfer mechanism engaging the bottom culture plate and transferring it out of the cassette.

In another aspect, a method is provided for stacking and handling nested culture plates in an automated culture plate handling instrument. The method includes the steps of:

(a) providing in the instrument a structure holding a stack of culture plates, the culture plates having features for nesting the plates relative to each other;

(b) providing a de-nesting feature in the structure causing the bottom culture plate in the stack to be held in the cassette in an off-set, de-nested condition relative to the adjacent culture plate above it;

(c) automatically removing the bottom culture plate from the cassette with a robotic transfer mechanism;

(d) the removing of the bottom culture plate causing the remaining culture plates in the stack of culture plates within the cassette to descend within the cassette, e.g., due to gravity, optionally with assistance from an external source such as a spring; and (e) wherein the said adjacent culture plate becomes the new bottom culture plate in the stack and wherein the de-nesting feature causes the new bottom culture plate to be held in a de-nested condition relative to its adjacent culture plate above it in the stack.

In one example embodiment, the steps (c), (d) and (e) repeat until the all of the culture plates have been removed from the holding structure The apparatus and methods of this disclosure may optionally have a feature for de-nesting the culture plate above the bottom culture plate from its upper adjacent culture plate in the stack.

BRIEF DESCRIPTION OF THE DRAWINGS

FIG. 2 is another perspective view of the cassette of FIG. 1. FIG. 2 shows the opening in the base of the cassette through which a culture plate is removed from the cassette via a robotic transfer mechanism.

DETAILED DESCRIPTION OF PREFERRED EMBODIMENT

Figure 1:
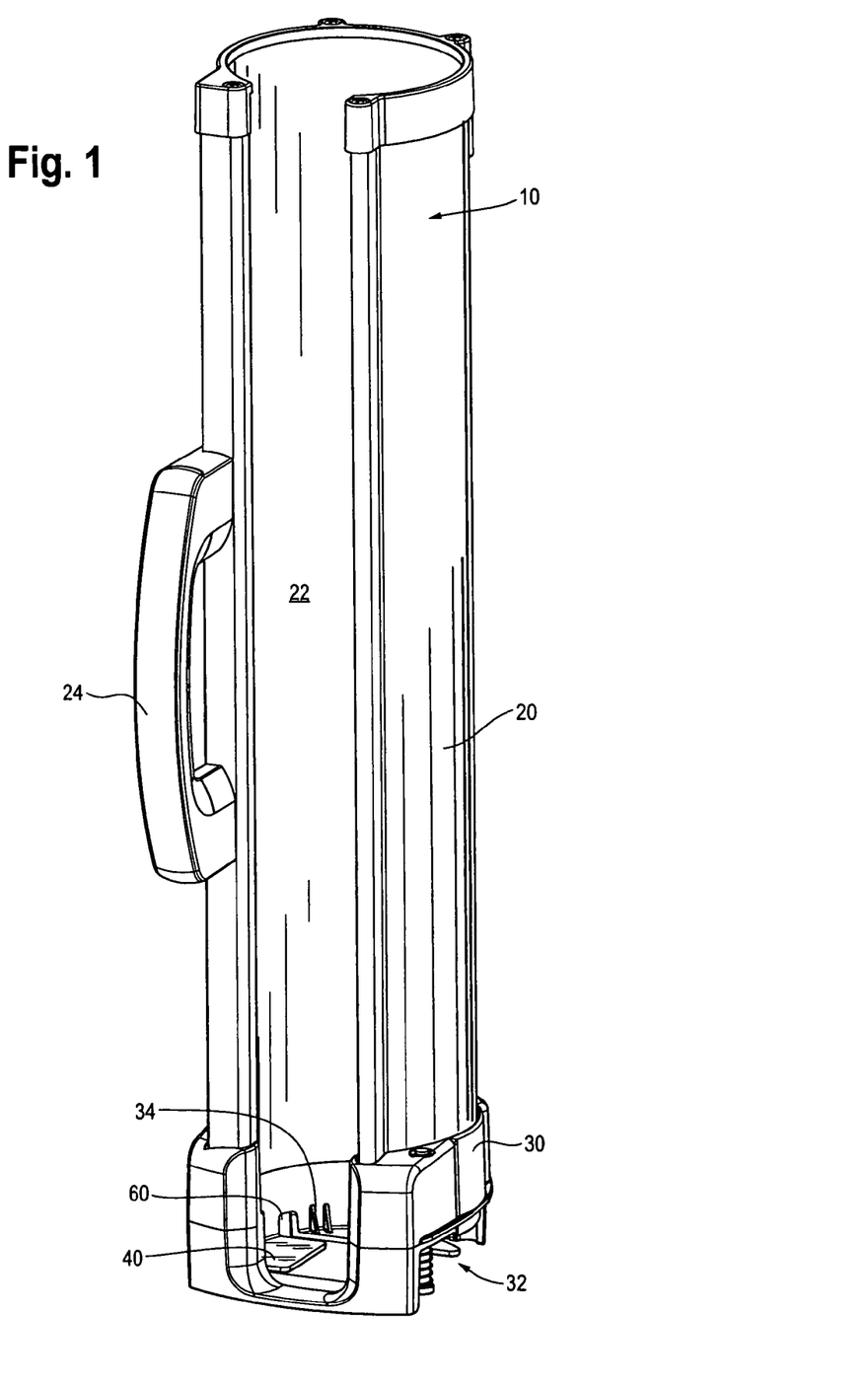
FIG. 1 is a perspective view of a holding structure in the form of a cassette having a de-nesting feature for de-nesting culture plates stacked within the cassette.
Figure 2:
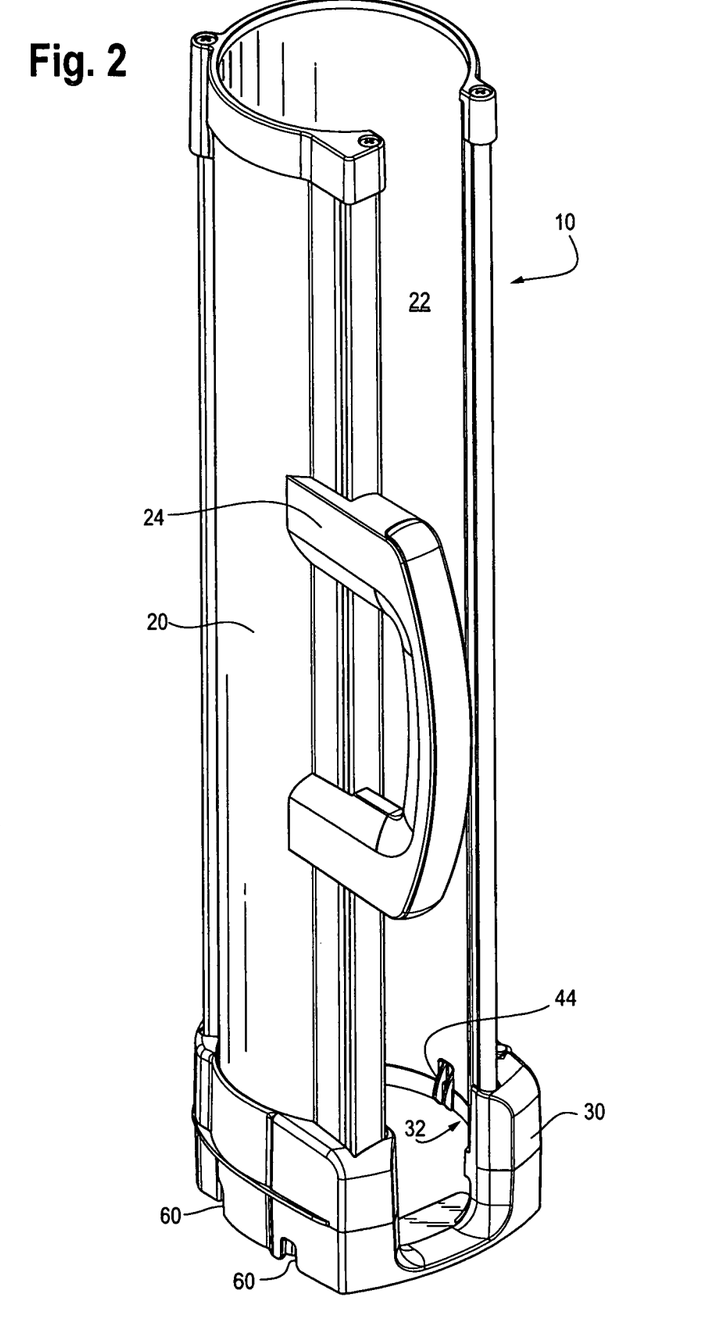
Figure 3:
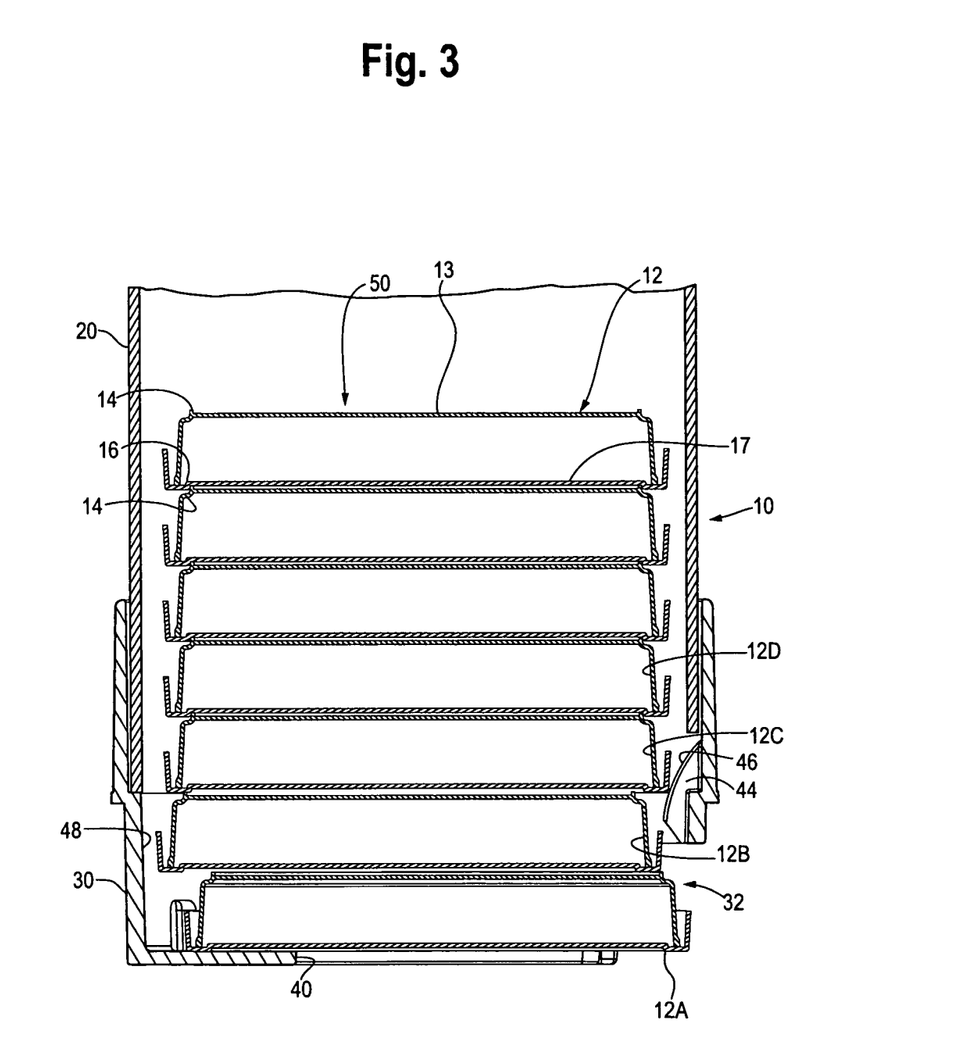
FIG. 3 is a cross-sectional view through the cassette of FIGS. 1 and 2, showing the de-nesting of the bottom plate from the plate above it. In the embodiment of FIGS. 1-3, the cassette also includes a de-nesting feature for de-nesting the second from the bottom plate from the plate above it.
Figure 6:
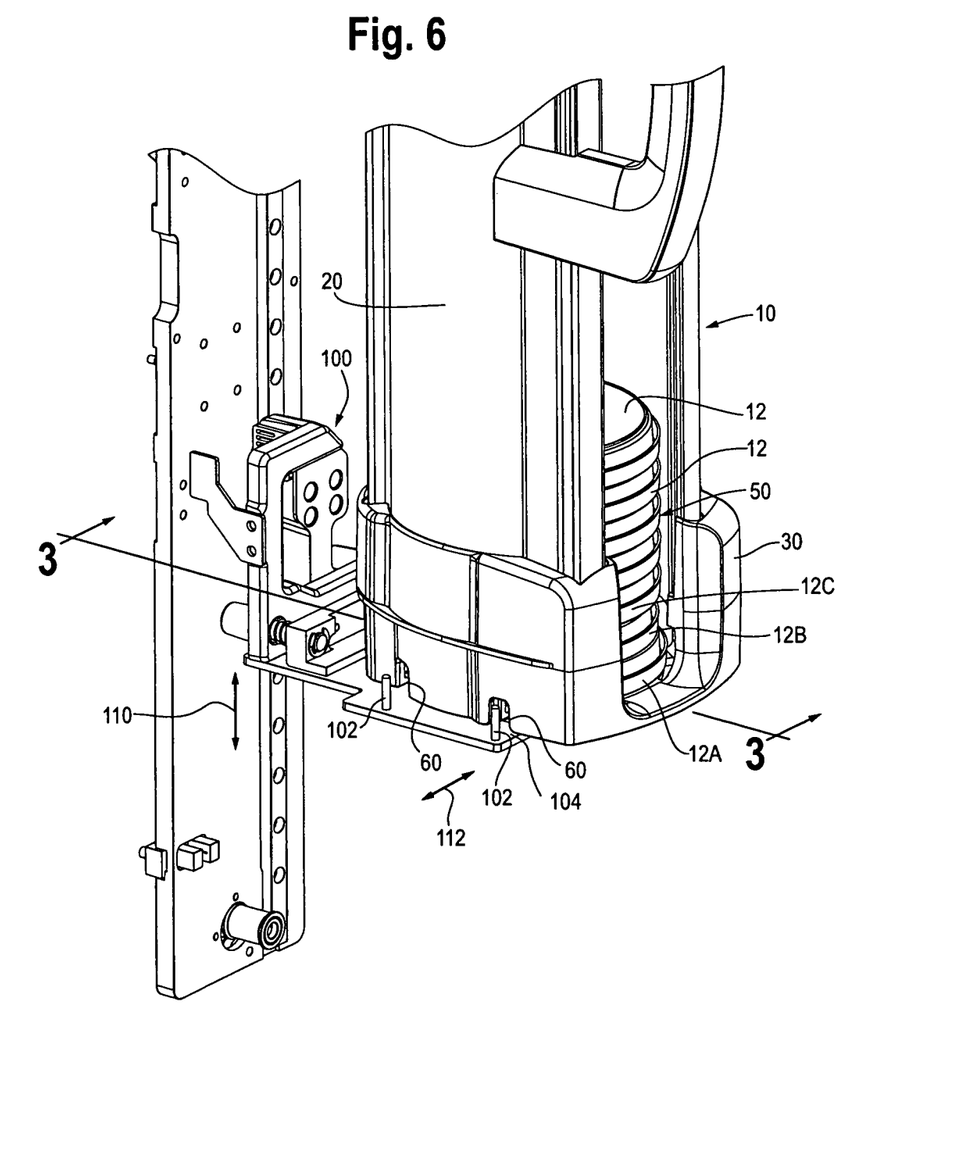
FIG. 6 is a view of the cassette of FIGS. 1-3 partially loaded with a stack of culture plates, showing the robotic transfer mechanism which slides the bottom culture plate in the stack out of the cassette.

Referring now to the drawings, FIGS. 1 and 2 are perspective views of a cassette 10 having a de-nesting feature for de-nesting culture plates stacked within the cassette 10. The culture plates 12 are shown in FIGS. 3 and 6 and are omitted from FIGS. 1 and 2 in order to show the features of the cassette 10. As best shown in FIGS. 3 and 6, the culture plates 12 contain nesting features wherein one culture plate is in a nested relationship with an adjacent culture plate when the plates are arranged in a stack 50. The plates 12 are shown in an upside down, stacked condition in the cassette 10 of FIG. 3.

The nesting feature of the plates 12 in the illustrated embodiment can be seen in FIG. 3, in which the bottoms 13 of the plates 12 include a slight projecting ridge feature 14 which nests with a corresponding recess 16 in the lid 17 of the adjacent plate. This nesting as shown in FIG. 3 promotes ease of handling of the plates 12 on the laboratory bench, but presents problems when a plate in a stack 50 of such plates 12 is to be extracted from the cassette by robotic plate handing equipment. (It should be noted that the design of the cassette would also work with plates that do not have a nesting feature. Also, the invention can be used when the plates are oriented in the stack right-side-up.)

Figure 7:
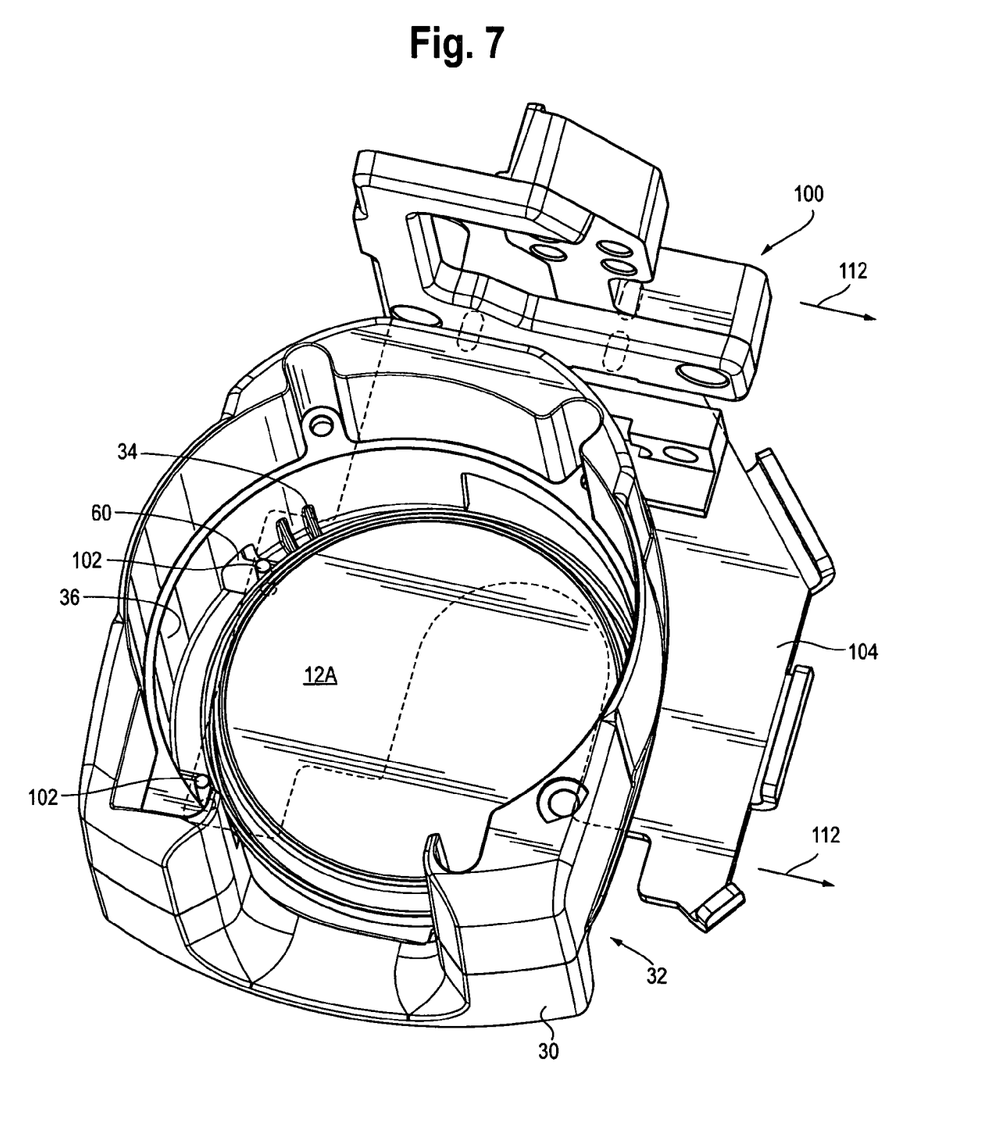
FIG. 7 is a perspective view showing the base of the cassette and the bottom culture plate held therein, with the robotic transfer mechanism of FIG. 6 shown partly in phantom lines. The arrows indicate the direction of movement of the robotic transfer mechanism when it removes the bottom plate from the cassette.

As best shown in FIGS. 1, 2 and 3, the cassette 10 includes an elongate tubular member or housing 20 for holding or containing a stacked arrangement of culture plates, as shown in FIGS. 3 and 6. The housing 20 has an opening 22 which permits ease of manually loading culture plates 12 into the housing and visual observation of the number of plates held within the cassette. Typically, the cassette 10 is loaded with culture plates off-line and then the operator places the loaded cassette into the associated plate handling instrument. The cassette has a handle 24 which the operator grasps to load the cassette into the plate handling instrument. The functionality of the plate handling instrument is not particularly relevant to this invention and so is omitted for the sake of brevity. The instrument includes a robotic transfer mechanism for removing a culture plate from the instrument. The robotic transfer mechanism is shown in FIGS. 6 and 7 and will be described subsequently in further detail.

It will also be noted that the invention can be used in situations where the cassette or other holding structure for holding a stack of plates remains a permanent part of the automated plate handling instrument. In this situation the user simply manually inserts the plates into the holding structure in the instrument.

The cassette 10 includes a base 30. The base can be integrally formed with the tubular housing 20 or can be a separate piece that fits into or is otherwise mechanically joined to the tubular housing 20. The de-nesting features of the illustrated embodiment are formed in the base 30 as will be described below. The base 30 defines an opening 32 wherein the bottom culture plate 12 in the stack of plates 23 may be withdrawn from the cassette 10.

Figure 5:
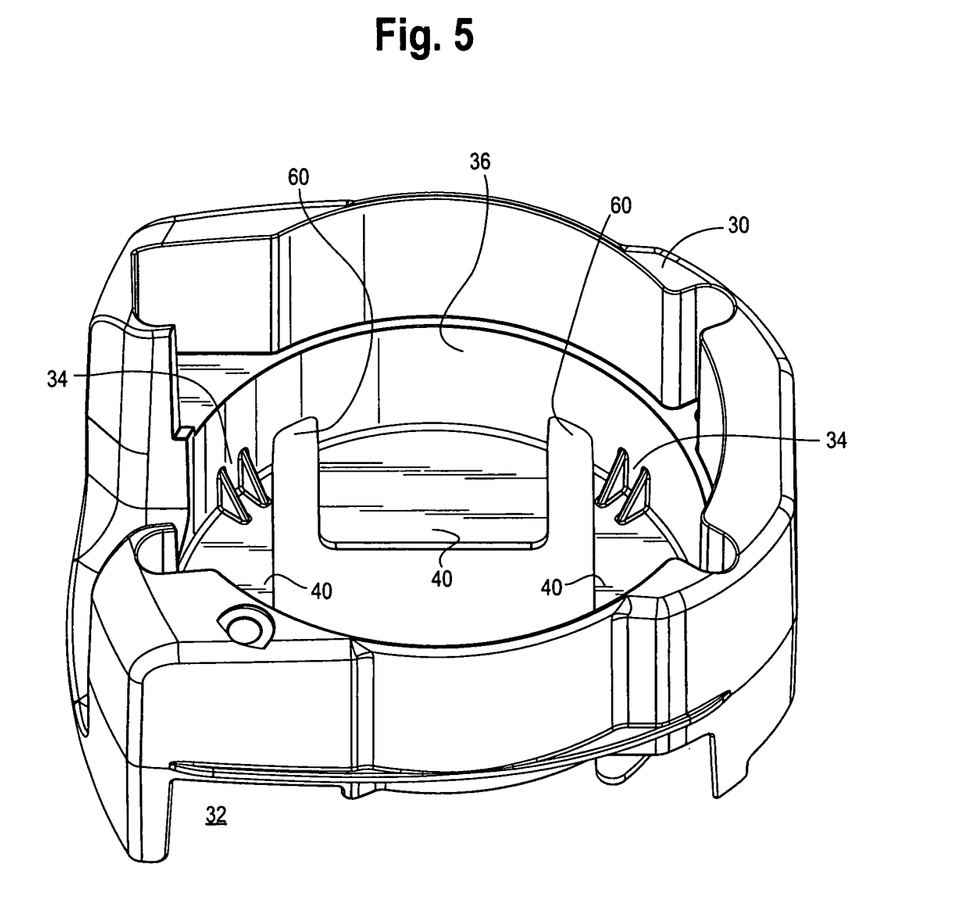
FIG. 5 is another isolated, perspective view of the base of the cassette of FIGS. 1-4.

In particular, the base 30 includes a feature in the form of ramps 34 best shown in FIG. 5 which operate to passively de-nest the bottom culture plate 12A (FIG. 3) from the adjacent culture plate 12B above it to thereby facilitate withdrawal of the bottom culture plate 12A from the base via the opening 32. Two sets of ramps 34 are provided for this purpose. The ramps 34 are sloped projections extending inwardly from the interior surface 36 of the base 30 which serve to move the plate 12A laterally relative to the plate 12B above it, thereby moving the plate 12A out of a nested condition with plate 12B, when the plate 12A moves past the ramps. The ramps 34 operate entirely passively. The operation of moving the plate 12A laterally into a de-nested condition relative to plate 12B happens when the plate at the bottom of the stack is withdrawn from the cassette by the robotic transfer mechanism and the stack of plates in the cassette drops, e.g., by means of gravity. As the plate 12A is moved vertically downwards by gravity, the ramps 34 serve to move the plate 12A laterally. The base 30 is constructed so as to provide clearance in the bottom of the base for the bottom plate 12 to sit flat on a plate support 40 formed in the base 30.

Figure 4:
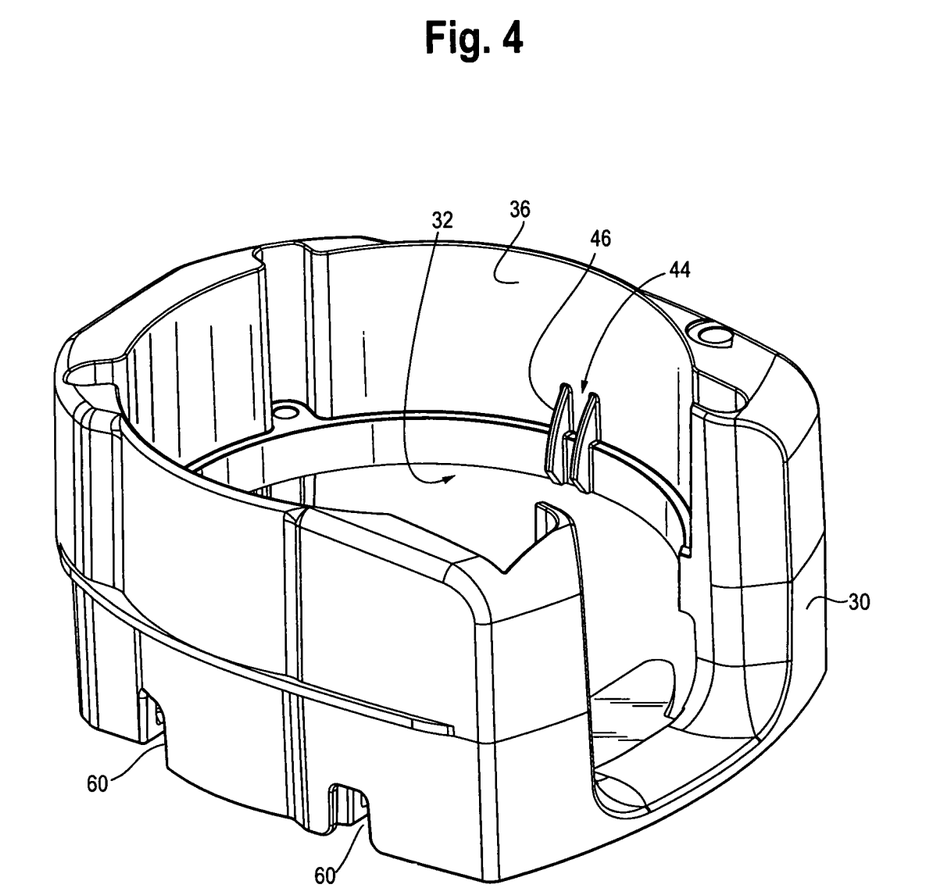
FIG. 4 is an isolated, perspective view of the base of the cassette of FIGS. 1-3.

The base 30 also includes a second feature to de-nest the culture plate 12B above the bottom culture plate 12A from its upper adjacent culture plate 12C in the stack 50. The feature to de-nest the culture plate 12B from culture plate 12C takes the form of a single ramp 44 formed in the interior surface 36 of the base, shown best in FIGS. 3 and 4. The ramp 44 serves to move the associated plate at its level (plate 12B) slightly laterally relative to the plate above it (plate 12C). The base 30 includes clearance at the elevation of ramp 44 (seen in FIG. 3 at 48) to allow the plate 12B to sit essentially level above the plate 12A and below plate 12C, but not in a nested condition with either plate. Thus, in the illustrated embodiment, the bottom culture plate 12A is in a de-nested condition relative to the culture plate above the bottom culture plate (plate 12B) and the culture plate 12B is in a de-nested condition relative to its upper adjacent culture plate 12C in the stack. As shown in FIG. 3, as the plate 12C drops within the stack 50 (due to the action of withdrawing of plate 12A from the bottom of the stack), the plate 12C rides down the surface 46 of the ramp 44 and is directed laterally slightly to the left (as seen in FIG. 3) such that it is de-nested from the plate above it. When plate 12A is withdrawn, plate 12B falls to the position previously occupied by plate 12A and is moved laterally to the right toward the opening 32 by ramps 34 (FIG. 5). Thus, plate 12C rides down the surface 46 of ramp 44 to the position of plate 12B, plate 12D and all the plates above it in the stack are lowered one position. The process of removing a plate, lowering of the plates in the stack by one position, and the de-nesting of the bottom plate and the plate above it continue until the entire cassette is emptied of plates.

The de-nesting feature preferably takes the form of a projection from the inner surface 36 of the base. The feature is shown as sloped ramps, which can be solid sliding surface or individual ridge like structures arranged in pairs or other groupings as shown in the drawings. Other types of projection features are possible. Whatever their construction, the de-nesting feature urges a culture plate to move in a lateral direction as the culture plate descends in the stack at the elevation of the de-nesting feature due to gravity and withdrawal of a culture plate from the bottom of the stack.

The bottom plate 12A in the stack of plates sits essentially level on a holding platform 40 of the base 30, seen best in FIG. 5. The base includes a pair of openings 60 through which pass a pair of pins 102 of a robotic transfer mechanism 100 seen best in FIGS. 6 and 7. In particular, the robotic transfer mechanism 100 includes a carriage 104 for supporting a plate and a pair of pins 102 extending upwards from the carriage 104 at one end thereof, as shown in FIG. 7. The entire transfer mechanism 100 is capable of moving up and down as indicated by the arrow 110 in FIG. 6 and from left to right and right to left as indicated by the arrow 112 in FIGS. 6 and 7.

To withdraw the plate 12A from the cassette 10, the robotic transfer mechanism 100 moves to the position shown in FIG. 6 and then translates to the right. The action of translating to the right in the direction of the arrow 112 in FIG. 6 causes the pins 102 to pass through the openings 60 in the base 30 of the cassette 10. The pins make contact with the edge of the plate 12A as seen in FIG. 7 and further movement to the right in the direction of the arrow 112 causes the pins 102 to slide the plate 12A through the opening 32, and onto the carriage 104. The carriage 104 acts as a support holding the plate 12A as the plate is carried by the robot transfer mechanism to downstream processing stations in an instrument incorporating the cassette and robotic transfer mechanism 100.

Once plate 12A is removed from the cassette, plate 12B falls by gravity to the bottom position within the cassette and is moved laterally by ramps 34 as explained previously out of a de-nested condition with respect to the plate above it. This action could be facilitated by use of a spring acting on the top plate of the stack biasing the stack in a downward direction. Provided sufficient clearance is maintained between the plates and the side of the cassette housing, a spring is typically not needed.

Figure 8:
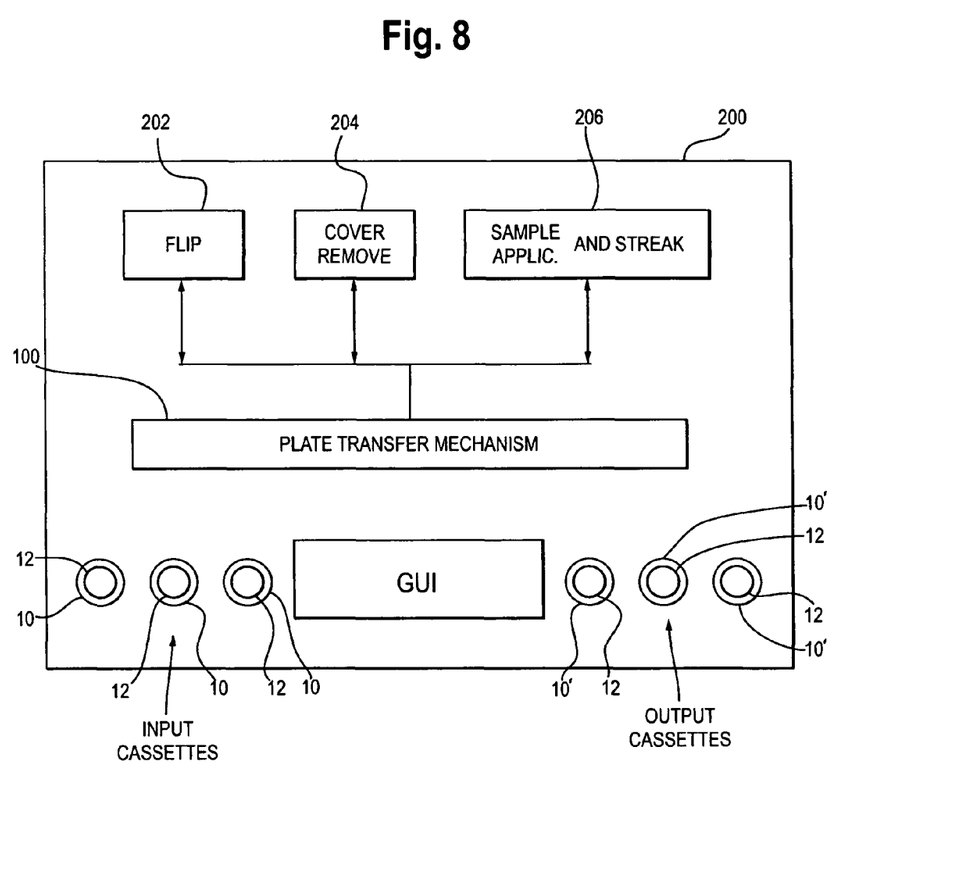
FIG. 8 is a schematic illustration of a plate handling instrument incorporating the cassette and robotic transfer mechanisms of FIG. 6-7.

An example of an instrument incorporating the de-nesting feature of the cassette 10 is shown in FIG. 8. The instrument 200 includes a plurality of the cassettes 10, each having the structure of FIGS. 1-7, which are loaded with culture plates 12 for processing. The robotic transfer mechanism 100 operates to withdraw a plate 12 from a cassette and send it to subsequent stations, e.g., a station 202 where the plate 12 is flipped over, a station 204 where the lid for the plate is removed, and a station 206 where a sample is applied to the culture medium contained within the plate and the sample medium is streaked. These stations 202, 204 and 206 are not particularly pertinent to this invention and take a variety of forms, including the forms described in the previously-referenced patent documents or the form of other instruments currently known in the art. After processing, the plates are loaded into output cassettes 10'. Loaded output cassettes are removed from the instrument and loaded into a separate incubator or incubated in situ.

These details of the instrument 200, and details related to handling of a sample, are omitted in order to not obfuscate the present disclosure.

From the above discussion, it will be appreciated that we have described an automated instrument 200 for processing culture plates 12, the instrument comprising at least one holding structure (e.g., cassette 10) for holding a plurality of culture plates 12 in a stacked arrangement 50 (FIG. 3, 6), the stacked arrangement of culture plates 12 including a bottom plate 12A. In the illustrated embodiment the cassette 10 includes a tubular member 20 for holding the stacked arrangement of culture plates in a vertical orientation (FIGS. 3, 6). However, other types of holding structures could be used. The holding structure includes a base 30, the base defining an opening 32 wherein the bottom culture plate 12A may be withdrawn from the cassette 10. The culture plates 12 contain nesting features (FIG. 3) wherein one culture plate is nested in relationship to an adjacent culture plate in the stacked arrangement, and wherein the base further comprises a feature 34 to de-nest the bottom culture plate 12A from the adjacent culture plate 12B thereby facilitating withdrawal of the bottom culture plate 12A from the base via the opening 32. The instrument includes a robotic transfer mechanism 100 engaging the bottom culture plate 12 via pins 100 and transferring it out of the cassette 10. In particular, the de-nesting performed by the sloped ramp features 34 serves to disrupt the nesting and de-couple the plates 12A and 12B, permitting the plate 12A to be withdrawn by a robotic transfer mechanism 100 without jamming.

As shown in FIG. 8, the instrument includes a plurality of cassettes 10. Each of the input cassettes 10 holds a culture plates in a stacked and nested arrangement. Each of the cassettes is the same as shown in FIGS. 1-7, and includes a tubular member 20 and a base 30 having an opening 32 and a feature 34 to de-nest the bottom culture plate from the adjacent culture plate in the stacked arrangement thereby facilitating withdrawal of the bottom culture plate from the base 30 via the opening 32.

It will also be appreciated that we have disclosed a method of stacking and handling nested culture plates 12 in an automated culture plate handling instrument 200. The method comprises the steps of:

(a) providing in the instrument 200 a holding structure (e.g. a cassette 10) holding a stack 50 of culture plates 12 (FIG. 6), the culture plates 12 having features (FIG. 3) for nesting the plates relative to each other;

(b) providing a de-nesting feature (34) in the holding structure 10 causing the bottom culture plate 12A in the stack 50 to be held in the cassette in an off-set, de-nested condition relative to the adjacent culture plate 12B above it (shown best in FIGS. 3, 5 and 6);

(c) automatically removing the bottom culture plate 12A from the holding structure 10 with a robotic transfer mechanism (see the description of FIGS. 6 and 7);

(d) the removing of the bottom culture plate causing the remaining plates in the stack 50 of culture plates to descend within the cassette 10, e.g., due to gravity (see the above discussion); and (e) wherein the adjacent culture plate 12B becomes the new bottom culture plate in the stack, and wherein the de-nesting feature 34 causes the new bottom culture plate 12B to be held in a de-nested condition relative to its adjacent culture plate above it 12C in the stack.

The steps (c), (d) and (e) are typically repeated until the all of the culture plates have been removed from the cassette. When the cassette is empty, it is removed from the instrument 200 and replaced with a newly loaded cassette 10.

In the above method, the method may further comprise the step of de-nesting the culture plate 12B above the bottom culture plate 12A from its upper adjacent culture plate 12C in the stack. See the above discussion of ramps 44 and FIG. 3.

In the preferred embodiments, the step of de-nesting the bottom culture plate, and the culture plate above the bottom culture plate is performed passively, as for example by the use of structural features formed in the base of the cassette and the operation of gravity causing the plates to move past the de-nesting features 34, 44 and being forced to move laterally relative to the plate above it.

While preferred embodiments have been described with particularity, persons having skill in this art will appreciate that variation from the specifics of the illustrated embodiments is possible without departure from the scope of the invention. This scope is to be determined by reference to the pending claims. For example, variation may be made to the specifics of the robotic transfer mechanism, the manner in which the plates are nested to each other, the orientation of the plates, the structure for holding a stack of plates, and the structure which causes the de-nesting to occur. For example, the principles of this invention can be applied to instruments which hold a stack of plates using four (typically) vertically arranged guide rods which define a region for receiving and holding a stack of plates. The guide rods could extend upwards from a base featuring the de-nesting ramps as disclosed herein. Alternatively, the base of the guide rods could be designed with features such that as a plate held by the guide rods moves to the lowest position in the stack the guide rods move the plate off-set from the plate above it to de-nest the plate.

We claim:

1. An apparatus for holding a plurality of culture plates in a stacked arrangement in which the culture plates are placed vertically above each other in a stack, the stacked arrangement of culture plates including a bottom plate in the stacked arrangement, wherein the culture plates contain nesting features wherein an upper portion of one culture plate is in a nested relationship with an adjacent culture plate by virtue of the upper portion being received within a bottom portion of the adjacent culture plate in the stacked arrangement, the apparatus comprising:
   a holder holding the stacked arrangement of culture plates;
   the holder having a base, the base defining an opening wherein the bottom culture plate may be withdrawn from the base;
   wherein the base further comprises a structure passively and completely de-nesting the bottom culture plate from the adjacent culture plate by moving the bottom culture plate laterally such that the upper region of the bottom culture plate is no longer received with the bottom portion of the adjacent culture plate while retaining the bottom culture plate within the holder thereby facilitating withdrawal of the bottom culture plate from the base via the opening.

2. The apparatus of claim 1, wherein the base further comprises a second structure to de-nest the culture plate above the bottom culture plate from its upper adjacent culture plate in the stack, whereby the bottom culture plate is in a de-nested condition relative to the culture plate above the bottom culture plate and whereby the culture plate above the bottom culture plate is in a de-nested condition relative to its upper adjacent culture plate in the stack.

3. The apparatus of claim 1, wherein the base is in the form of a tube and includes an inner surface receiving the culture plates and wherein the structure comprises a projection from the inner surface, the structure urging a culture plate to move in a lateral direction as the culture plate descends in the stack at the elevation of the structure due to gravity and withdrawal of a culture plate from the bottom of the stack.

4. The apparatus of claim 3, wherein the projection comprises a sloped ramp.

5. The apparatus of claim 1, wherein the base further comprises openings for receiving a robotic transfer mechanism and sliding the bottom culture plate out of the opening.

6. The apparatus of claim 1, wherein the base and the holder holding the stack of culture plates comprises separate pieces.

7. The apparatus of claim 1, wherein the holder holding the stack of plates comprises an elongate tubular member.

8. The apparatus of claim 1, wherein the holder holding the stack of plates comprises a plurality of vertically arranged guide rods.

9. An automated instrument for processing culture plates, the instrument comprising:
   a holder for holding a plurality of culture plates in a stacked arrangement in which the culture plates are placed vertically above each other in a stack, the stacked arrangement of culture plates including a bottom plate, the holder holding the stacked arrangement of culture plates in a vertical orientation;
   a base for the holder, the base defining an opening wherein the bottom culture plate may be withdrawn from the holder;
   wherein the culture plates contain nesting features wherein an upper portion of one culture plate is nested in relationship to an adjacent culture plate by virtue of the upper portion being received within a bottom portion of the adjacent culture plate in the stacked arrangement, and
   wherein the base further comprises a structure passively and completely de-nesting the bottom culture plate from the adjacent culture plate by moving the bottom culture plate laterally such that the upper region of the bottom culture plate is no longer received with the bottom portion of the adjacent culture plate while retaining the bottom culture plate within the holder thereby facilitating withdrawal of the bottom culture plate from the base via the opening; and
   a robotic transfer mechanism engaging the bottom culture plate and transferring it out of the base.

10. The instrument of claim 9, wherein the instrument comprises a plurality of cassettes, each holding culture plates in a stacked and nested arrangement, and wherein each of the cassettes includes a tubular member and a base having an opening and a structure to de-nest the bottom culture plate from the adjacent culture plate in the stacked arrangement thereby facilitating withdrawal of the bottom culture plate from the base via the opening.

11. The instrument of claim 9, wherein the holder comprises an elongate tubular member.

12. The instrument of claim 11, wherein the tubular member is removable from and insertable into the instrument.

13. The instrument of claim 9, wherein the holder comprises a plurality of vertically oriented guide rods.

\* \* \* \* \*